US00PP10177P

United States Patent [19]

Zaiger et al.

[11] Patent Number: Plant 10,177

[45] Date of Patent: Jan. 6, 1998

[54] PEACH TREE 'KAWEAH'

[76] Inventors: Chris Floyd Zaiger, 929 Grimes Ave.; Gary Neil Zaiger, 1907 Elm Ave.; Leith Maire Gardner, 1207 Grimes Ave.; Grant Gene Zaiger, 4005 California Ave., all of Modesto, Calif. 95358

[21] Appl. No.: 745,080

[22] Filed: Nov. 7, 1996

[51] Int. Cl.[6] ..... A01H 5/00

[52] U.S. Cl. ..... Plt./43.2

[58] Field of Search ..... Plt./43.2

*Primary Examiner*—James R. Feyrer

[57] ABSTRACT

A new and distinct variety of peach, *Prunus persica*, tree which has the unique combination of desirable features that are outstanding in a new variety:

1. Heavy and regular production of large size fruit.
2. Fruit with good flavor and eating quality.
3. Relatively uniform size fruit throughout the tree.
4. Fruit holding firm on the tree 7 to 8 days after maturity (shipping ripe).
5. Fruit with good handling and shipping quality.
6. Fruit with a high degree of attractive red skin color.
7. Having a vigorous upright growth.

1 Drawing Sheet

ORIGIN OF THE VARIETY

The present new variety of peach tree was originated by us in our experimental orchard located near Modesto, Calif., from a first generation cross between two selected seedlings field identification numbers 29G591 and 38G470. The maternal parent (29G591) originated as a selected seedling from open pollinated O'Henry Peach (U.S. Plant Pat. No. 2,964). seed. The pollen parent (38G470) originated from a first generation cross between Autumn Glory Peach (non-patented) and Fantasia Nectarine (non-patented). A large group of theses first generation seedlings were maintained and grown under close observation by us, during which time one such seedling, which is the present variety, exhibited especially desirable fruit characteristics and was selected for asexual reproduction and commercialization.

ASEXUAL REPRODUCTION OF THE VARIETY

Asexual reproduction of the new and distinct variety of peach tree was by budding, as performed by us in our experimental orchard located near Modesto, Calif., and shows that all characteristics of the tree and its fruit run true to the original tree and are established and transmitted through succeeding asexual propagations.

SUMMARY OF THE VARIETY

Our new and distinct variety of peach tree is of large size, vigorous, upright growth, and a regular and productive bearer of large, yellow flesh, freestone fruit with good flavor and eating quality. The fruit is further characterized by being relatively uniform in size throughout the tree, having good shipping and storage quality, and a high degree of attractive red skin color. In comparison to the O'Henry Peach (U.S. Plant Pat. No. 2,964) the tree of the new variety produces fruit that are more round in shape, more uniform in size throughout the tree, have a greater degree of attractive red skin color and are approximately 3 days earlier in maturity.

PHOTOGRAPH OF THE VARIETY

The accompanying color photographic illustration shows typical specimens of the foliage and fruit of the presnet new peach variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of peach tree, its flowers, foliage and fruit, as based on observations of specimens grown near Modesto, Calif., with color terminology (except those in common terms) in accordance with Reinold Color Atlas by A. Kornerup and J. H. Wanscher.

Tree:
- *Size.*—Large.
- *Vigor.*—Vigorous.
- *Growth.*—Upright.
- *Density.*—Medium dense.
- *Bearer.*—Regular.
- *Production.*—Productive.

Trunk:
- *Size.*—Medium to large.
- *Texture.*—Medium shaggy.
- *Color.*—Hair brown to brown (5-E-4) to (5-F-6).

Branches:
- *Size.*—Medium.
- *Surface.*—Smooth to medium rough, varies with age of growth.
- *Lenticels.*—Numerous. Small in size.
- *Color.*—Light brown to brown, varies with maturity.

Leaves:
- *Size.*—Large. Average length 7¼". Average width 1¾".
- *Form.*—Lanceolate, pointed.
- *Thickness.*—Medium.
- *Margin.*—crenate.
- *Petiole.*—Medium length. Medium thickness.
- *Texture.*—Smooth.
- *Glands.*—Number varies from 1 to 5. Average number 3. Reniform. Medium size. Located on base of leaf blade and upper portion of petiole.
- *Color.*—Upper surface — green to dark green (29-F-6) to (28-F-8 ). Lower surface — light green to brackish green (29-E-6) to (29-E-7).

Flower buds:
- *Size.*—Medium to large.

*Length.*—Medium.
*Form.*—Plump.

Flowers:
*Size.*—Large, showy.
*Blooming period.*—Date of first bloom: Mar. 1, 1994. Date of full bloom: Mar. 5, 1994. Varies slightly with climatic conditions.
*Pollen.*—Present, self-fertile.
*Color.*—Pink.

Fruit:
*Maturity when described.*—Firm ripe.
*Date of first picking.*—Jul. 26, 1994.
*Date of last picking.*—Jul. 31, 1994.
*Size.*—Large. Average diameter axially 3". Average transversely in suture plane 3⅛".
*Form.*—Nearly globose. Slightly flattened at stem.
*Suture.*—Shallow, nearly rounded. Extends from base to apex.
*Ventral surface.*—Nearly rounded, varies from rounded to slightly lipped.
*Cavity.*—Rounded, slightly elongated in suture plane. Average depth ¾". Average breadth 1".
*Base.*—Retuse.
*Apex.*—Usually rounded, varies from rounded to slight apical point.

Flesh:
*Ripens.*—Evenly.
*Texture.*—Firm.
*Fibers.*—Few, small, tender.
*Juice.*—Moderate.
*Aroma.*—Moderate.
*Amygdalin.*—Undetected.
*Flavor.*—Good.
*Eating quality.*—Good.
*Color.*—Butter yellow to maize ellow (4-A-5) to (4-A-6). Pit cavity, rose red to red (12-A-8) to (12-C-8). Slight bleeding from pit cavity into flesh.

Skin:
*Thickness.*—Medium.
*Texture.*—Medium, tenacious to flesh.
*Tendency to crack.*—None.
*Down.*—Moderate amount. Medium in length.
*Color.*—Maize yellow to melon yellow ground color (4-A-6) to (5-A-6). Nearly overspread with red to orient red (9-B-8) to (10-C-8).

Stone:
*Type.*—Freestone.
*Size.*—Medium to large. Average length 1½". Average width 1". Average breadth ⅝".
*Form.*—Usually obovate. Varies from obovate to ovate.
*Base.*—Rounded.
*Apex.*—Usually slight point, varies from slight point to rounded.
*Surface.*—Irregularly furrowed toward apex. pitted toward base, pits vary from rounded to elongated.
*Sides.*—Equal to unequal.
*Tendency to split.*—None.
*Color.*—Reddish brown to brown. (9-D-5) to (9-E-6).

Use: Dessert.
*Market.*—Local and long distance.

Keeping quality: Good.
Shipping quality: Good.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of peach tree, substantially as illustrated and described, characterized by its large size, vigorous, upright growth and a regular and productive bearer of large, yellow flesh, freestone fruit with good flavor and eating quality; the fruit is further characterized by being nearly uniform in size throughout the tree, having firm flesh with good handling and shipping quality and, in comparison to the fruit of the O'Henry Peach (U.S. Plant Pat. No. 2,964), are more round in shape, more uniform in size throughout the tree with a greater degree of attractive red skin color and are approximately 3 days earlier in maturity,

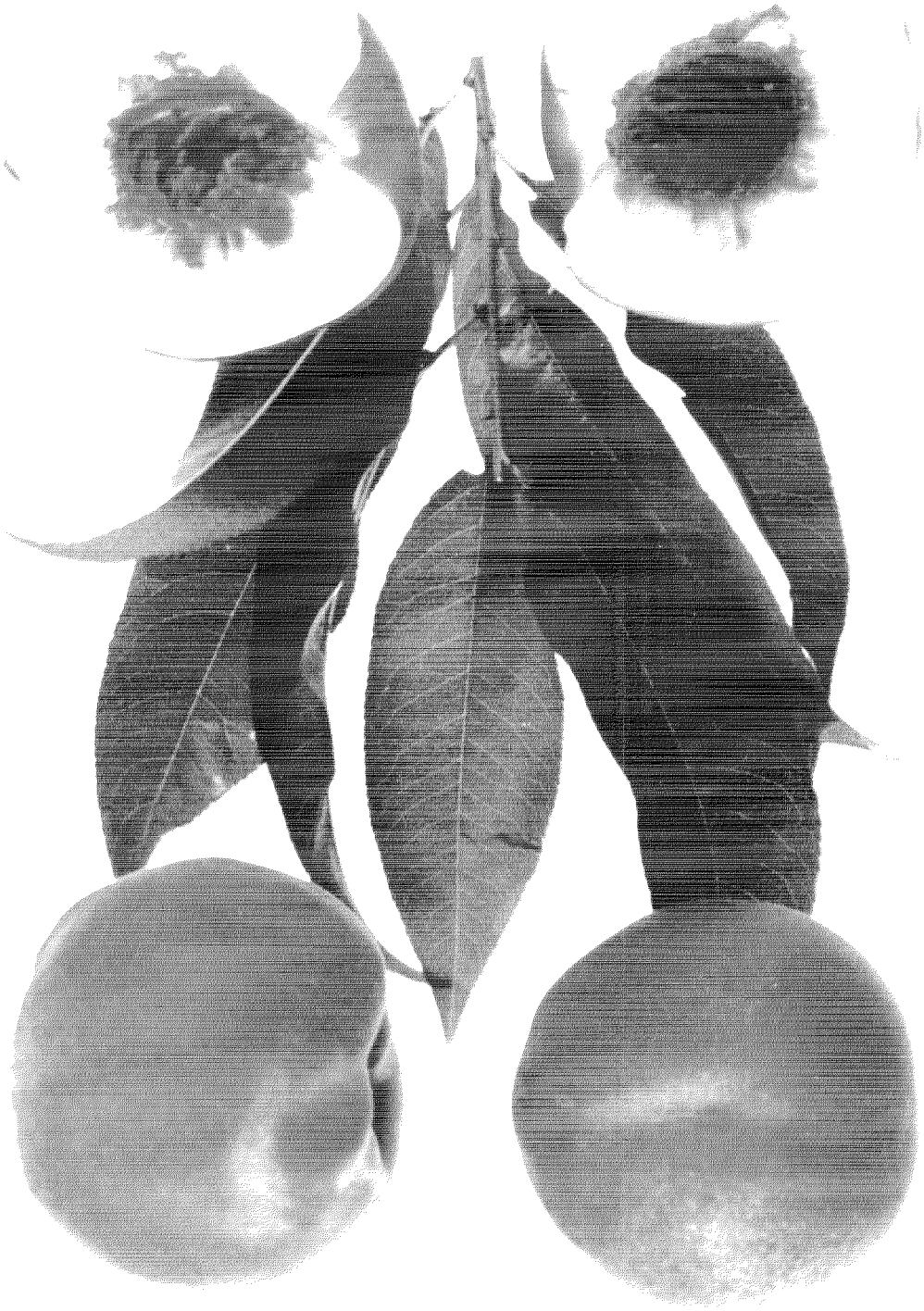

* * * * *